United States Patent [19]

Stephens

[11] Patent Number: 4,529,708
[45] Date of Patent: Jul. 16, 1985

[54] ASSAY FOR THE DETERMINATION OF CREATININE

[75] Inventor: Thomas W. Stephens, Indianapolis, Ind.

[73] Assignee: American Monitor Corporation, Indianapolis, Ind.

[21] Appl. No.: 482,753

[22] Filed: Apr. 7, 1983

[51] Int. Cl.³ .............................................. G01N 33/70
[52] U.S. Cl. ....................................... 436;98; 436/175
[58] Field of Search ............................ 436/97, 98, 175

[56] References Cited

U.S. PATENT DOCUMENTS

| 3,894,843 | 7/1975 | Jarvis | 436/98 |
| 4,111,657 | 9/1978 | Denney et al. | 436/98 |

FOREIGN PATENT DOCUMENTS

| 29718 | 3/1980 | Japan | 436/98 |

OTHER PUBLICATIONS

Tagesson et al., Clinical Chemistry, vol. 26, No. 3, 1980, p. 520.
Osberg et al., Clinical Chemistry, vol. 24, No. 7, pp. 1196-1197, 1978.
Wako, Chemical Abstracts, vol. 96, 1982, No. 96: 196193q.
Wako, Chemical Abstracts, vol. 94, 1981, No. 94: 135591e.
Lolekha et al., Clinica Chimica Acta, 107(1980) 97-104.
Daugherty et al., Clinical Chemistry, vol. 24, No. 2, 1978, pp. 392-393.

Primary Examiner—Arnold Turk
Attorney, Agent, or Firm—Marilyn L. Amick

[57] ABSTRACT

An improved colorimetric assay method and reagent composition for the quantitative determination of creatinine in biological fluid specimens in the presence of protein, in which the specimen is reacted directly with an alkaline picrate reagent composition which contains an iron chelator, preferably ethylenediaminetetraacetic acid, thereby significantly suppressing interference from bilirubin and improving reagent stability.

3 Claims, No Drawings

ASSAY FOR THE DETERMINATION OF CREATININE

BACKGROUND OF THE INVENTION

1. Field of the Invention

This invention relates to an improved assay method and reagent composition for determining creatinine levels in body fluids, and more particularly to a colorimetric method which is performed directly on serum and other fluids without deproteinization.

2. Nature and Significance of Accurate Creatinine Determinations

It has been recognized for almost a century that the measurement of creatinine is of vital medical significance, and even today, the most widely used kidney function test in clinical practice is the estimation of glomerular filtration rate by measurement of the creatinine level in serum and urine specimens. Tests or assays that measure such creatinine levels are major criteria in determining whether kidney disease is present and, if present, the extent to which it is present.

Creatinine is synthesized in the body at a fairly constant rate from creatine, which is produced during muscle contractions from creatine phosphate. Creatinine in the blood is then removed by filtration through the glomeruli of the kidney for excretion in the urine. Since the excretion of creatinine in healthy individuals is independent of diet and thus relatively constant, the creatinine clearance test is one of the most sensitive tests for measuring glomerular filtration rate, and the concentration of creatinine in the serum depends almost entirely upon its rate of excretion by the kidney. In kidney disease, therefore, creatinine levels in the blood are elevated, while the creatinine clearance, or urine levels, are diminished.

3. Discussion of the Prior Art

Prior art methods date as far back as 1886 when Jaffe (*Z. Physiol. Chem.* 10:391, 1886) described the formation of a red color when creatinine was reacted with picrate in an alkaline solution. Today, this classic Jaffe reaction remains the basis for a majority of the current creatinine assay methods.

Although the Jaffe reaction achieves a measurable result, it has long been recognized that the reaction suffers a significant drawback in its lack of specificity for measuring creatinine in serum and urine. More particularly, a number of other substances which are normally present in serum and urine also form a red color with picrate or otherwise interfere with the reaction, thereby causing inaccurate and misleading results. Most of these substances cause a positive interference by increasing the amount of color formation. Such substances include, for example, protein, glucose, ascorbate, acetoacetate, pyruvate and other alpha-keto acids. On the other hand, bilirubin in the presence of protein causes a negative interference, or falsely low results.

To overcome the problems of non-specific color formation, numerous methods have been developed which remove the interfering substance by some type of sample pretreatment, the most commonly performed pretreatment methods being protein precipitation and removal by filtration, treatment with Lloyd's reagent, or removal of protein by dialysis through a membrane.

However, such pretreatment methods are cumbersome and time-consuming. Furthermore, with the exception of protein removal by dialysis, pretreatment methods have a particular disadvantage in that they do not easily lend themselves to automation, which has become a virtual necessity in meeting the demands of today's clinical laboratories. Additionally, pretreatment in many cases may solve only a portion of the non-specificity problems or may even create additional specificity problems.

In 1971, Bartels and Bohmer (*Clin. Chem. Acta* 32:81, 1971) and Cook (*Clin. Chim. Acta* 32:485, 1971) proposed the measurement of creatinine in the presence of protein by measuring the rate of color development of the classic Jaffe reaction, i.e., kinetic measurement. Although many different means have been attempted in past years to improve the specificity of the Jaffe reaction, the most popular means of improving specificity of creatinine assays has been the use of kinetic methods based on the Jaffe reaction. Denney and Long (U.S. Pat. No. 4,111,657, issued Sept. 5, 1978) suppressed protein interference in a kinetic creatinine assay by the incorporation of dimethylsulfoxide in an alkaline picrate reagent. Although their method achieved several important advantages over earlier attempts, their modifications left unsolved the problem of the negative interference from bilirubin present in serum specimens, i.e. icteric samples. Many investigators have recently studied and attempted to correct for this negative interference, which appears to exist in virtually all of today's popularly used creatinine assay methods which are carried out in the presence of protein.

Two investigators, Tagesson and Rebel (*Clin. Chem.* 26:520, 1980), quite apart from attempting to solve bilirubin interference, attempted to resolve a problem of drift (a continuous gradual increase in results) in certain continuous flow creatinine methods. (Continuous flow methods rely upon the separation of protein from the specimens by use of a semi-permeable membrane.) Tagesson and Rebel postulated that calcium was precipitating in the cuvette in which optical density was measured and added EDTA to prevent the precipitation of calcium and thus reduce the drift causing increasing creatinine values. The present invention also incorporates EDTA, however achieving benefits quite in contrast to those of Tagesson and Rebel. In fact, the benefits of the present invention would be quite unnoticed and unappreciated in continuous flow methods since protein, and substances which are bound to protein, including bilirubin, are separated and removed from the samples being assayed.

SUMMARY OF THE INVENTION

Accordingly, it is therefore a general object of the present invention to provide a novel reagent composition and assay method for the determination of creatinine in fluid samples in the presence of protein. A more particular object of the present invention is to provide a method which employs a kinetic measurement of the reaction of creatinine in an alkaline picrate reagent. A further object is to provide a reagent and assay method in which there is negligible interference from bilirubin. Yet a further object is to provide a method which is readily adaptable for use with the variety of automated and semi-automated laboratory instrumentation in current use today. Another object is to provide a reagent composition with enhanced stability. These and other objects, features, and advantages will be apparent from the following description of the presently preferred embodiments of the present invention.

It has been discovered that when an agent which binds or chelates iron is included in a buffered alkaline picrate solution, the objects and goals of the present invention are achieved. The preferred iron chelator is ethylenediaminetetraacetic acid (EDTA); however, N-hydroxyethylethylenediaminetetraacetic acid (HEDTA) and ethylene glycol-bis($\beta$-amino-ethyl ether)-N,N'-tetraacetic acid (EGTA) have also been found to be useful. The buffered alkaline picrate solution is preferably of the nature as described and set forth in the aforementioned Denney and Long patent, i.e., dimethylsulfoxide is also included in the reagent to suppress protein interference. Optionally, surface active agents known to be useful in suppressing turbidity may also be included.

EDTA is added to the reagent in the preferred amount of at least about 0.5 millimoles per liter. This quantity of EDTA has been found to be sufficient to adequately suppress negative bilirubin interference in specimens containing as much as 20 milligrams per deciliter (mg/dl) of bilirubin. (The minimum concentration of bilirubin necessary to visibly discolor serum is approximately 3 mg/dl, while normal bilirubin levels are generally less than 1 mg/dl.)

To use the reagent composition of the present invention to perform an assay for creatinine, a sample of serum, urine, or other fluid is combined with the reagent. The rate of formation of the colored picramate complex is measured photometrically at a wavelength between about 480 nm and 530 nm. Calibration of the assay is accomplished by similarly treating an equal volume of a standard or reference material containing a known amount of creatinine.

Although the present invention can be practiced by additions of the desired ingredients to the sample individually or in the form of one or more reagent combinations, it is customary and convenient for laboratory and other analytical personnel to use pre-formulated compositions, or reagents, which are generally known as "test kits", and which are available on a commercial basis from various manufacturers. A kit may contain one or more pre-formulated reagents and appropriate calibration and quality control materials, or the kit may be in the form of one or more pre-formulated reagents packaged individually or in bulk form for a specific intended use.

With respect to the present invention, it is preferable that the test kit contain two separate, pre-formulated reagents, one containing picrate and the other containing an alkaline buffer. Either or both reagents may also contain additional desired ingredients such as surfactants, antimicrobial agents, and others that will be known to those skilled in the art. With respect to the present invention, the EDTA may be added to either reagent, but solubility has been found to be better if included in the alkaline buffer.

DESCRIPTION OF THE PREFERRED EMBODIMENTS

The specific embodiments of the present invention detailed herein are provided to enable an analyst skilled in the art to understand and make reagent compositions and to perform an assay according to the novel concepts and achievements of the present invention.

EXAMPLE 1

Reagent Preparation

An alkaline buffer reagent is prepared by combining the following substances in the amount indicated in sufficient deionized water to make a total volume of one liter:
20.5 milliliters sodium hydroxide, 50% solution
416 milligrams EDTA, tetrasodium The resulting solution should be approximately 0.4 N sodium hydroxide.

A picrate reagent is prepared by combining the following substances in the amount indicated in sufficient deionized water to make a total volume of one liter:
4.2 grams picric acid
219 grams dimethylsulfoxide
4 milliliters ® 25-3S
(Neodol is a trademark of Shell Chemical Company, Houston, Tex. Neodol 25-3S is an ethoxysulfate surfactant.)

A diagnostic reagent for the determination of creatinine is then prepared by combining equal quantities of the alkaline buffer and the picrate reagents. The final reagent thus prepared has been found to retain its utility for at least thirty (30) days, while the alkaline buffer and picrate reagents stored separately are expected to retain their utility for at least two years.

EXAMPLE 2

Determination of Creatinine

To perform an assay for creatinine, 4.0 milliliters of the reagent and 150 microliters of the sample to be assayed are mixed together. The rate of increase in absorbance (A) of the reaction mixture is then measured optically at a wavelength of about 510 nm. For calibration, standard or reference material containing a known amount of creatinine is similarly treated.

To calculate the amount of creatinine in the sample, divide the change in absorbance at 510 nm per minute ($\Delta A_{510}$) of the assayed sample by the $\Delta A_{510}$ of the calibrator, then multiply the result thus obtained by the known amount of creatinine in the calibrator.

EXAMPLE 3

Determination of Creatinine

Using an automated chemical analyzer capable of performing mathematical comparisons involving rate reactions, an amount of the sample to be assayed and an amount of the reagent are combined in the preferred ratio of 1 part sample to 20 parts of the reagent. The rate of increase in absorbance at 510 nm is then measured and compared to the rate observed with a calibrator of known creatinine concentration. The KDA ® analyzer has been used in carrying out this embodiment of the present invention. (KDA is a registered trademark of American Monitor Corporation.)

EXAMPLE 4

Reagent Preparation

An alkaline buffer reagent is prepared by combining the following substances in the amount indicated in sufficient deionized water to make a total volume of one liter:
9.2 milliliters sodium hydroxide, 50% solution
416 milligrams EDTA, tetrasodium The resulting solution should be approximately 0.18 N sodium hydroxide.

A picrate reagent is prepared as described above in Example 1.

A diagnostic reagent for the determination of creatinine is then prepared by combining equal quantities of the alkaline buffer and the picrate reagents. The final reagent thus prepared has been found to retain its utility for at least thirty (30) days, while the alkaline buffer and picrate reagents stored separately are expected to retain their utility for at least two years.

EXAMPLE 5

Determination of Creatinine

Using an automated chemical analyzer capable of performing mathematical comparisons involving rate reactions, 40 microliters of the sample to be assayed are combined with 1.0 milliliter of the reagent, or any combination that will provide a preferred ratio of 1 part sample to 25 parts reagent. The rate of increase in color at 500 nm is then measured and compared to the rate observed with a calibrator of known creatinine concentration. The Parallel ® analytical system has been used in carrying out this embodiment of the present invention. (Parallel is a registered trademark of American Monitor Corporation.)

Although a final EDTA concentration of 0.5 millimoles per liter of prepared diagnostic reagent is presented in the preferred embodiments set forth herein, amounts up to 5.0 millimolar or greater may be used in the practice of the present invention. The beneficial effects derived from additional amounts of EDTA, however, do not appear to increase proportionately, and 0.5 millimolar has been found to be an adequate concentration to meet the requirements of most clinical situations.

Other substances known to bind iron have also been found to be useful in the practice of the present invention. For example, 0.5 millimolar quantities of ethyleneglycol-bis($\beta$-amino-ethyl ether)-N,N'-tetraacetic acid (EGTA), and N-hydroxyethylethylenediaminetetraacetic acid (HEDTA) have been found to also significantly suppress or eliminate bilirubin interference.

Furthermore, optical measurements of the reaction need not necessarily be limited to absorbance-measuring techniques. It is conceivable that transmittance-measuring and even reflectance-measuring techniques may also be employed. Other modifications and perturbations to the foregoing embodiments will be apparent to those skilled in the art and are not to be considered beyond the scope of the novel concepts of the present invention.

What is claimed is:

1. A method for the determination of creatinine in a protein-containing fluid, comprising the steps of:
   (a) combining a sample of said protein-containing fluid with a reagent to form a reaction mixture, said reagent comprising:
      (i) an alkalinizing agent,
      (ii) picrate, and
      (iii) a substance which binds iron in an amount sufficient to suppress interference from bilirubin; and
   (b) optically measuring the change in said reaction mixture.

2. A method as recited in claim 1, wherein the substance which binds iron is selected from the group consisting of ethylenediaminetetraacetic acid (EDTA), N-hydroxyethylethylenediaminetetraacetic acid (HEDTA), and ethyleneglycol-bis ($\beta$-amino-ethyl ether)-N,N'-tetraacetic acid (EGTA).

3. A method as recited in claim 2, wherein the amount of the substance which binds iron is at least about 0.5 millimoles per liter.

* * * * *